United States Patent
Sobe

(10) Patent No.: US 10,111,599 B2
(45) Date of Patent: Oct. 30, 2018

(54) SHIELDED TWISTED PAIR OF CONDUCTORS USING CONDUCTIVE INK

(71) Applicant: St. Jude Medical International Holding S.à r.l., Luxembourg (LU)

(72) Inventor: Lior Sobe, Kadima (IL)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 338 days.

(21) Appl. No.: 14/790,541

(22) Filed: Jul. 2, 2015

(65) Prior Publication Data

US 2015/0374254 A1 Dec. 31, 2015

Related U.S. Application Data

(62) Division of application No. 13/753,117, filed on Jan. 29, 2013, now Pat. No. 9,101,046.

(51) Int. Cl.
*A61B 5/042* (2006.01)
*H05K 9/00* (2006.01)
(Continued)

(52) U.S. Cl.
CPC ............ *A61B 5/0422* (2013.01); *A61B 5/062* (2013.01); *A61B 5/068* (2013.01); *A61B 5/6847* (2013.01);
(Continued)

(58) Field of Classification Search
CPC ....... H04R 25/00; A61B 5/0422; A61B 5/062; A61B 5/068; A61B 5/6847; H05K 1/0245; H05K 3/4685; H05K 9/0073
(Continued)

(56) References Cited

U.S. PATENT DOCUMENTS 5,036,160 A   7/1991   Jackson
5,168,876 A   12/1992  Quedens et al.
(Continued)

FOREIGN PATENT DOCUMENTS

CN   1200010 A     11/1998
CN   201114981 Y   9/2008
(Continued)

OTHER PUBLICATIONS

English Language Translation of Office Action (2014/80004517.6).
(Continued)

*Primary Examiner* — Dah-Wei D. Yuan
*Assistant Examiner* — Andrew Bowman
(74) *Attorney, Agent, or Firm* — Dykema Gossett PLLC

(57) ABSTRACT

An apparatus for transmitting electrical signals is disclosed. The apparatus includes a substrate and a twisted pair of conductors located on the substrate. The twisted pair of conductors has a first layer comprising conductive material, a second layer comprising nonconductive material, and a third player comprising conductive material. The first layer has a plurality of segments separated by a plurality of gaps. The second layer is positioned in said gaps and electrically insulates a portion of the segments positioned within the gaps. The third layer is positioned over the second layer. The third layer is configured to electrically connects an end of one segment to an end of another segment. The twisted pair of conductors formed by the three dimensional structure comprises two electrically isolated conductors twisted about each other.

14 Claims, 9 Drawing Sheets

FIG.5

(51) Int. Cl.
 H05K 1/02 (2006.01)
 A61B 5/00 (2006.01)
 A61B 5/06 (2006.01)
 H05K 3/46 (2006.01)
 A61B 6/12 (2006.01)
 A61B 5/0402 (2006.01)
 A61B 6/00 (2006.01)

(52) U.S. Cl.
 CPC ......... *H05K 1/0245* (2013.01); *H05K 3/4685* (2013.01); *H05K 9/0073* (2013.01); *A61B 5/0402* (2013.01); *A61B 5/6851* (2013.01); *A61B 5/6852* (2013.01); *A61B 6/12* (2013.01); *A61B 6/487* (2013.01); *A61B 2562/0223* (2013.01); *A61B 2562/125* (2013.01); *A61B 2562/182* (2013.01); *A61B 2562/222* (2013.01); *A61B 2562/227* (2013.01); *H05K 2201/0715* (2013.01); *H05K 2201/097* (2013.01); *H05K 2203/0548* (2013.01); *H05K 2203/30* (2013.01)

(58) Field of Classification Search
 USPC ........................................................ 381/322
 See application file for complete search history.

(56) References Cited

U.S. PATENT DOCUMENTS

| | | | |
|---|---|---|---|
| 5,199,432 A | 4/1993 | Quedens et al. | |
| 5,357,051 A | 10/1994 | Hwang | |
| 5,373,843 A | 12/1994 | Quedens et al. | |
| 5,646,368 A | 7/1997 | Muyshondt et al. | |
| 5,878,487 A | 3/1999 | McMillan, II et al. | |
| 6,233,476 B1 | 5/2001 | Strommer et al. | |
| 6,498,944 B1 | 12/2002 | Ben-Haim et al. | |
| 6,788,967 B2 | 9/2004 | Ben-Haim et al. | |
| 7,167,378 B2 | 1/2007 | Yamada | |
| 7,229,437 B2 | 6/2007 | Johnson et al. | |
| 7,271,985 B1 | 9/2007 | Buhler et al. | |
| 7,386,339 B2 | 6/2008 | Strommer et al. | |
| 8,147,486 B2 | 4/2012 | Honour et al. | |
| 8,221,408 B2 | 7/2012 | Johnson et al. | |
| 8,704,102 B2 | 4/2014 | Duce et al. | |
| 2005/0241854 A1 | 11/2005 | Mehr et al. | |
| 2005/0283059 A1 | 12/2005 | Iyer et al. | |
| 2006/0215375 A1 | 9/2006 | Burhance et al. | |
| 2007/0299471 A1 | 12/2007 | Hisanori | |
| 2010/0022950 A1 | 1/2010 | Anderson et al. | |
| 2010/0163282 A1 | 7/2010 | Tagi et al. | |
| 2010/0200276 A1 | 8/2010 | Karikalan | |
| 2010/0307798 A1 | 12/2010 | Izadian | |
| 2011/0051965 A1* | 3/2011 | Beck | H04R 25/608 |
| | | | 381/322 |
| 2011/0255249 A1 | 10/2011 | Lee | |
| 2011/0270081 A1 | 11/2011 | Burg et al. | |
| 2012/0029287 A1 | 2/2012 | Wieters | |
| 2012/0055257 A1 | 3/2012 | Shaw-Klein | |
| 2012/0172842 A1 | 7/2012 | Sela et al. | |
| 2012/0265012 A1 | 10/2012 | Segawa | |
| 2014/0012130 A1 | 1/2014 | Jacobsen et al. | |

FOREIGN PATENT DOCUMENTS

| | | |
|---|---|---|
| CN | 102110501 A | 6/2011 |
| CN | 102332332 A | 1/2012 |
| DE | 10157678 A1 | 5/2003 |
| JP | H04-288135 A | 10/1992 |
| JP | 2002118333 | 4/2002 |
| JP | 2005137456 A | 6/2005 |

OTHER PUBLICATIONS

English Language Abstract of CN1200010A.
Kam et al., "A New Twisted Differential Line Structure on High-Speed Printed Circuit Boards to Enhance Immunity to Crosstalk and External Noise," Institute of Electrical and Electronics Engineers—Microwave and Wireless Components Letters, vol. 13, No. 9, Sep. 2003.
Kahn, "The M³D Aerosol Jet System, an Alternative to Inkjet Printing for Printed Electronics," Winter 2007. Retrieved from the internet: URL:http://organicandprintedelectronics.com.
English Language Abstract H04-288135.
English Language Abstract for CN 102110501A.
English Language Abstract for CN 102332332A.
English Language Abstract for CN 201114981Y.
English Language Translation of Office Action (201480004517.6).
English Language Translation of Office Action, dated Jun. 6, 2017 (Japanese Application No. 2015554292).
English Language Abstract for JP 2005137456A.

* cited by examiner

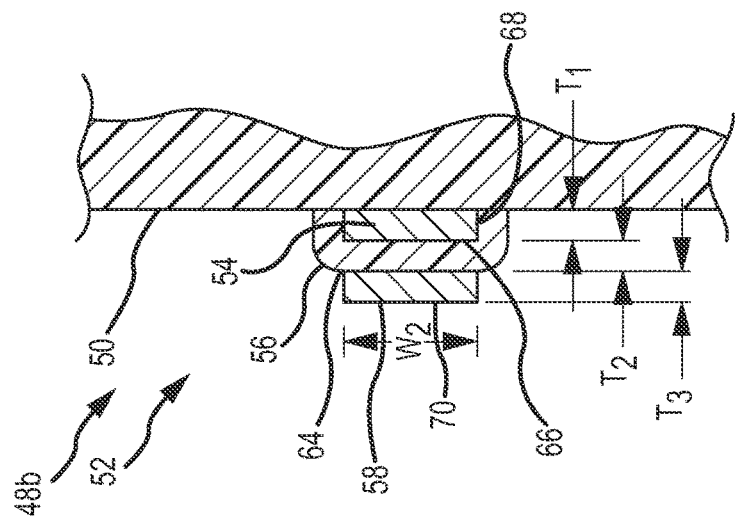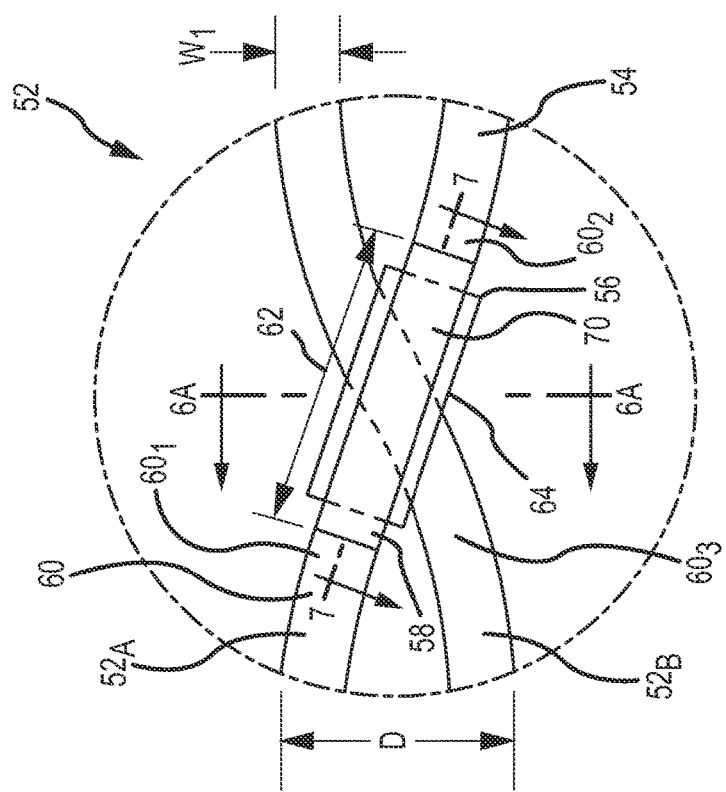

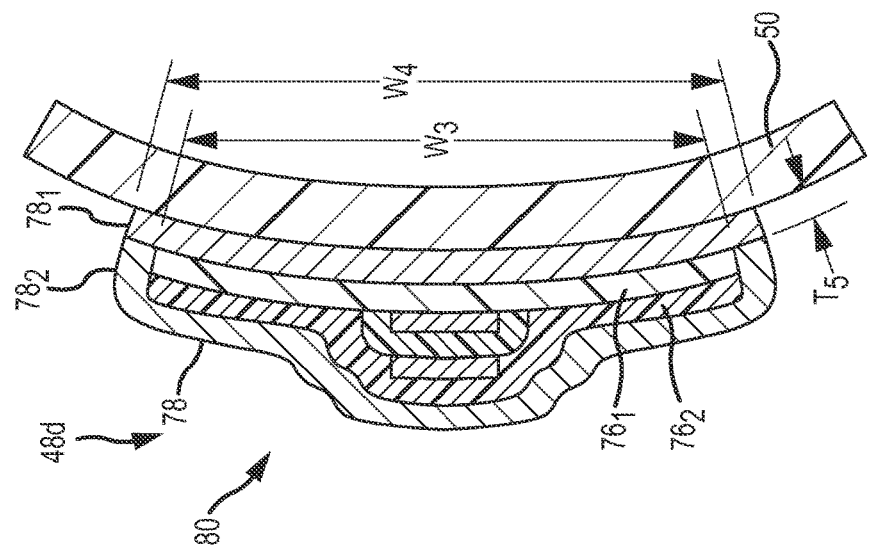
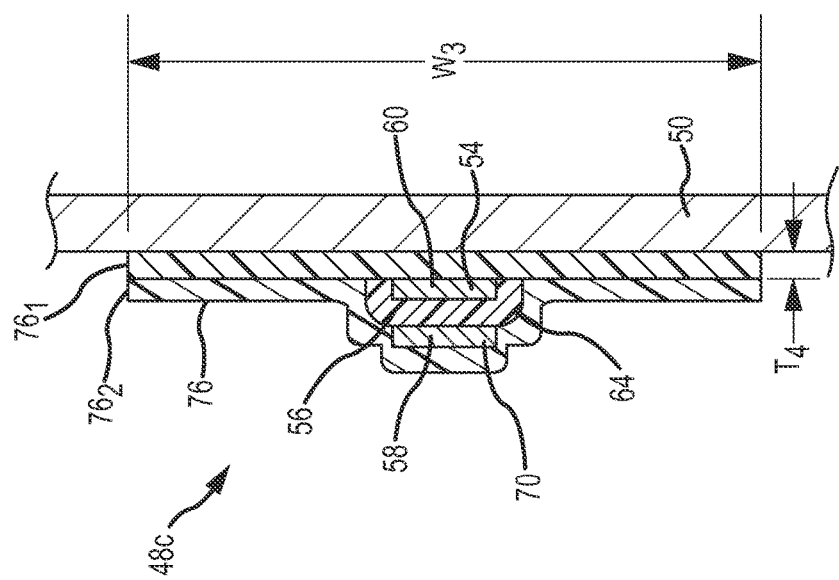

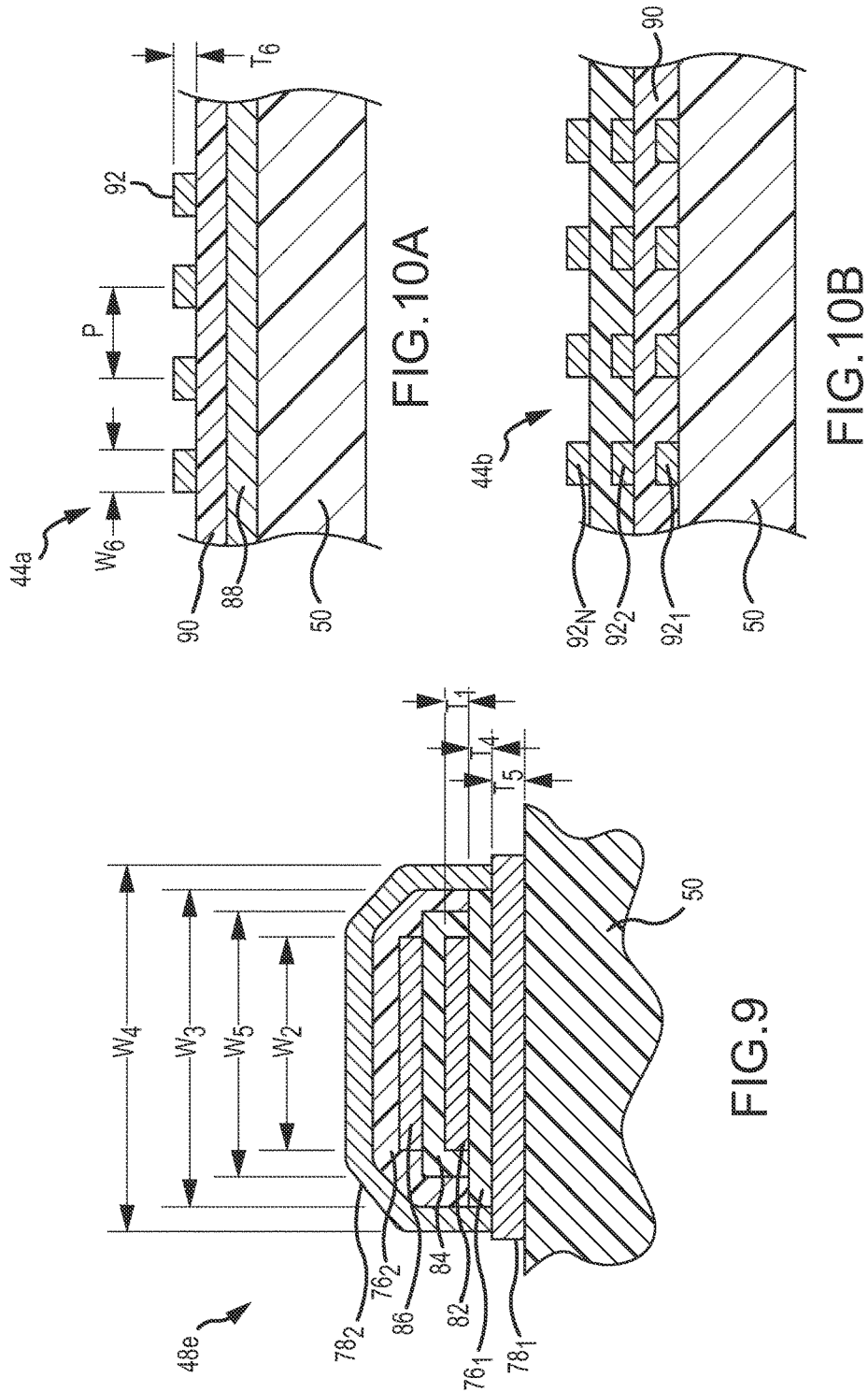

SHIELDED TWISTED PAIR OF CONDUCTORS USING CONDUCTIVE INK

CROSS-REFERENCE TO RELATED APPLICATIONS

This application is a division of U.S. application Ser. No. 13/753,117, filed 29 Jan. 2013 (the '117 application), now pending. The '117 application is hereby incorporated by reference as though fully set forth herein.

BACKGROUND a. Field of the Disclosure

The instant disclosure relates generally to formed electrical conductors having various layers of electrically conductive and electrically nonconductive materials.

b. Background

Various diagnostic and therapeutic procedures in or on the body of a patient, such as in the circulatory system, the gastrointestinal tract, the brain vessels, the bronchial tree or the like may be performed or facilitated by inserting medical devices into a body lumen and thereafter navigating the diagnostic or therapeutic medical devices to the target anatomical site. Electrically operated objects on a distal portion of the medical device may be utilized to facilitate the diagnostic, therapeutic, and navigational functions of the medical device. A proximal portion of the medical device may be operatively connected to a control unit which electrically communicates with the objects located on the distal portion.

To provide an electrical infrastructure for transmitting electrical signals, very small cables, such as but not limited to, shielded twisted pair of wires, may be utilized to connect electrically operated objects located on the distal portion of the medical device to the proximal portion of the medical device. For example, shielded twisted pair of wires are well known in the art for providing the benefit of reducing electromagnetic interference and may be used to connect the distal portion to the proximal portion of the medical device.

The foregoing discussion is intended only to illustrate the present field and should not be taken as a disavowal of claim scope.

BRIEF SUMMARY

In an embodiment, an apparatus for transmitting electrical signals may include a substrate and a twisted pair of conductors located on the nonconductive substrate. The twisted pair of conductors has a first layer comprising conductive material, a second layer comprising nonconductive material, and a third layer comprising conductive material. The first layer has a plurality of segments separated by a plurality of gaps. The second layer is positioned in the gaps and electrically insulates a portion of the segments positioned within the gaps. The third layer is positioned over the second layer. The third layer is configured to electrically connect an end of one segment to an end of another segment. The twisted pair of conductors formed by the three dimensional structure comprises two electrically separate conductors twisted about each other.

In an embodiment, an apparatus may comprise a substrate, a circuit layer, and a shield. The circuit layer may be located on the substrate. The circuit layer may have a conductor layer comprising conductive material, and an insulator comprising a lower insulator layer and an upper insulator layer. The conductor layer may be located between the lower insulator layer and the upper insulator layer. The shield may have a lower shield layer and an upper shield layer. The circuit layer may be located between the lower shield layer and the upper shield layer.

In an embodiment, a method for manufacturing an electrical infrastructure of a medical device may comprise forming a base layer, forming a masking layer, and forming a bridge layer. The base layer may comprise conductive material, formed in a predefined pattern on a surface of the medical device. The masking layer may comprise nonconductive material formed directly over a portion of the first layer of conductive material. The bridge layer may comprise conductive material formed directly over a portion of the first layer of conductive material and a portion of the masking layer.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 5 is an enlarged view of a portion of the electrical infrastructure of FIG. 4 which generally illustrates an embodiment of a twisted pair of conductors.

FIG. 6A is a cross-sectional view taken substantially along lines 6A-6A in FIG. 5.

FIG. 6B is a cross-sectional view of an embodiment of an insulated twisted pair of conductors.

FIG. 6C is a cross-sectional view of an embodiment of a shielded twisted pair of conductors.

FIG. 9 is a cross-sectional view of an embodiment of a three dimensional formed pair of conductors.

FIGS. 10A-B are cross-sectional side views of a portion of a position sensor coil of the medical device of FIG. 3.

DETAILED DESCRIPTION

Figure 1:
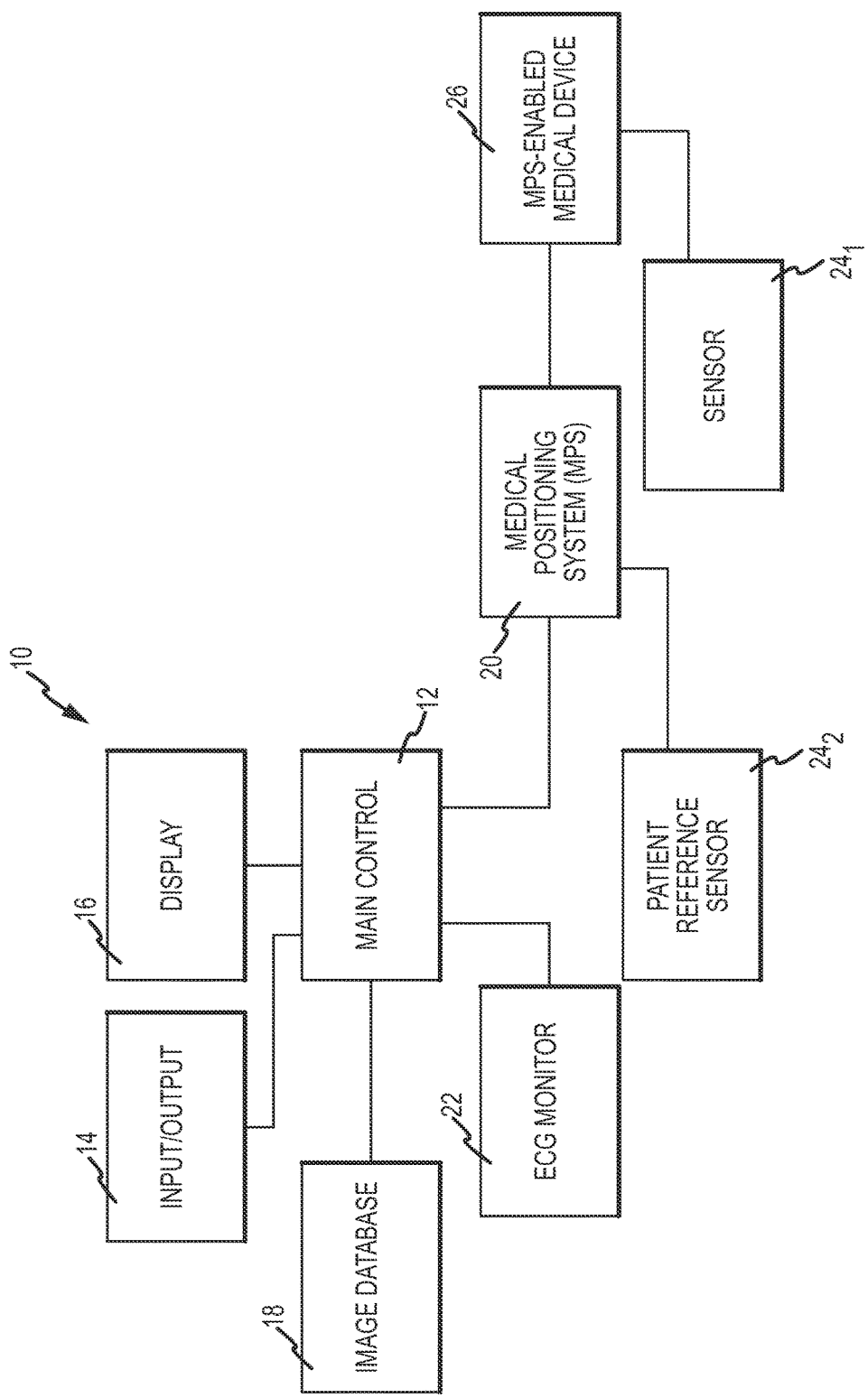
FIG. 1 is a schematic and block diagram view of a system demonstrating an environment in which a medical device having a formed electrical infrastructure may be used.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Before proceeding with a detailed description of a formed electrical infrastructure, a general description of an exemplary system in which a medical device 26 having such a formed electrical infrastructure 44 may be used is set forth below. As will be described hereinafter, embodiments of such an electrical infrastructure are configured generally for transmitting electrical signals in a medical device, for example, so as to connect electrically operated objects located on the distal portion of the medical device to the proximal portion of the medical device. Embodiments of such an electrical infrastructure may have similar properties as a shielded twisted pair of wires, for example, for providing the benefit of reducing electromagnetic interference. In addition, embodiments of such an electrical infrastructure may provide improvements relative to a shielded twisted pair of wires, which may be characterized as being relatively expensive to manufacture, relatively hard to handle due to their size, relatively mechanically sensitive, and in some instances too large to implement in medical devices having limited space without affecting the medical device's mechanical properties. Finally, embodiments of such an electrical infrastructure may be located directly on a surface of the medical device.

Referring now to the drawings wherein like reference numerals are used to identify identical or similar components in the various views, FIG. 1 is a block diagram view of a system 10 in which a medical device 26 having a formed electrical infrastructure 44 may be used. System 10 as depicted includes a main electronic control unit 12 (e.g., including one or more electronic processors) having various input/output mechanisms 14, a display 16, an optional image database 18, a localization system such as a medical positioning system (MPS) 20, an electrocardiogram (ECG) monitor 22, one or more MPS location sensors respectively designated $24_1$ and $24_2$, and an MPS-enabled medical device 26 which itself includes one and optionally more MPS location sensors, shown in exemplary fashion as having one such sensor $24_1$. Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Figure 2:
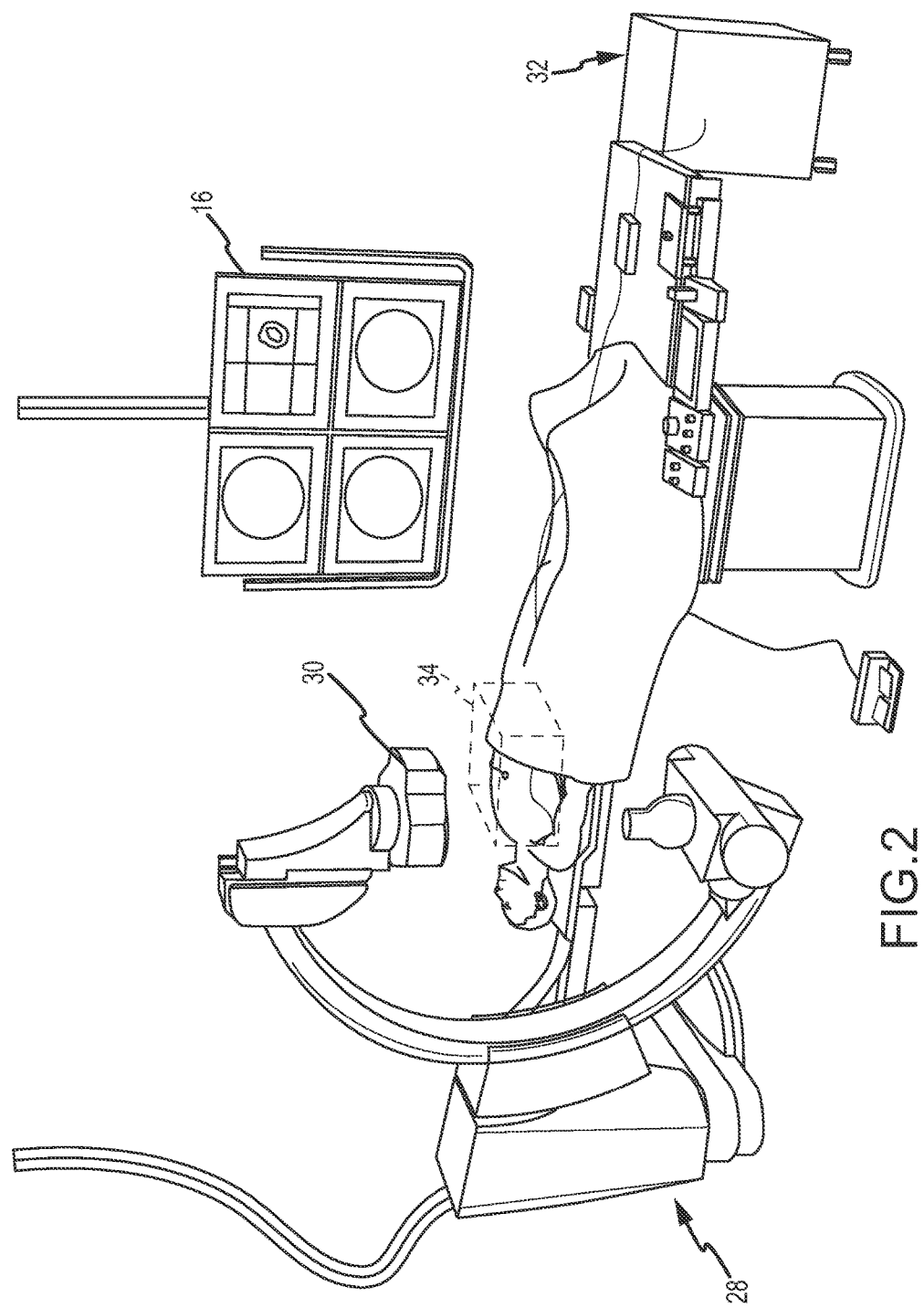
FIG. 2 is a diagrammatic view of an exemplary catheter-lab environment in which the system of FIG. 1, particularly a medical device having a formed electrical infrastructure may be used.

FIG. 2 is a diagrammatic view of system 10 as incorporated into a larger system, namely, a catheter lab. More specifically, system 10 is shown as being incorporated into a fluoroscopic imaging system 28, which may include commercially available fluoroscopic imaging components. It should be understood that while embodiments may be used in the catheter-lab environment to be described below, this is exemplary only and not limiting in nature. MPS 20 includes a magnetic transmitter assembly (MTA) 30 and a magnetic processing core 32 for determining location (P&O) readings. MTA 30 is configured to generate the magnetic field(s) in and around the patient's chest cavity, in a predefined three-dimensional space identified as a motion box 34. MPS sensors $24_i$ as described above are configured to sense one or more characteristics of the magnetic field(s) and when the sensors are in motion box 34, each generate a respective signal that is provided to magnetic processing core 32. Processing core 32 is responsive to these detected signals and is configured to calculate respective P&O readings for each MPS sensor $24_i$ in motion box 34. Thus, MPS 20 enables real-time tracking of each sensor $24_i$ in three-dimensional space.

The positional relationship between the image coordinate system and the MPS reference coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used. One exemplary embodiment of a MPS 20 will be described in greater detail below in connection with FIG. 11.

As described above and generally illustrated in FIGS. 1 and 2, the medical device 26 may require an electrical infrastructure in order to electrically connect objects located at a distal end portion of the medical device 26, such as one or more location sensors $24_i$, to a connector or the like at a proximal end portion of the medical device 26. The proximal end portion of the medical device 26 can then be electrically connected various apparatus (e.g., MPS 20 or main control unit 12) to establish electrical communication between the various apparatus and the objects.

Figure 3:
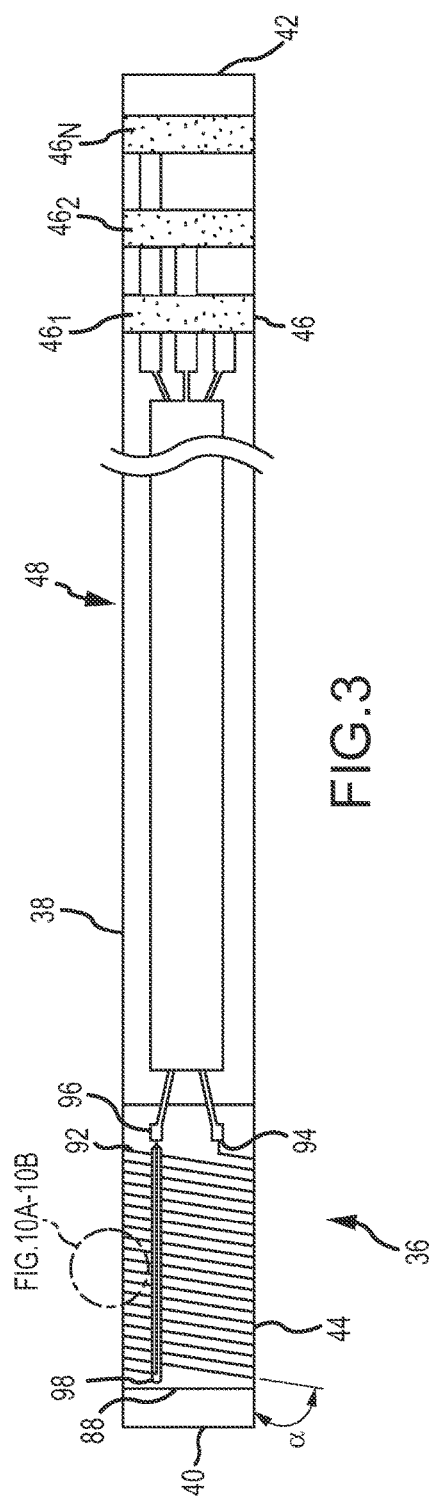
FIG. 3 is a diagrammatic top view of a medical device having an embodiment of a formed electrical infrastructure.

FIG. 3 is a diagrammatic top view, with portions broken away, of a medical device 36 having a first embodiment of an electrical infrastructure, designated infrastructure 48. The medical device 36 can be used in the system 10 that was shown and described in connection with FIGS. 1 and 2. Medical device 36 may include an elongate tubular body 38 having a distal end 40 and a proximal end 42. In various embodiments, the medical device 36 may comprise devices such as a catheter or a guidewire. The medical device 36 may further include an electrically-operated object, such as a location sensing coil 44. The location sensing coil 44 may be located at the distal end 40 of the medical device 36, although variations as to the electrical function performed by the object as well as its location are possible. The location sensing coil 44 may comprise an electromagnetic field-based positioning device, such as a magnetic field sensing coil 44 configured to produce a signal from which a sensor location can be determined (e.g., by the MPS 20). The determined sensor location may be used to facilitate various tracking, navigation, orientation, and other location-based or location-enabled functions of MPS 20.

The medical device 36 may further include an electrical connector or the like disposed at the proximal end 42. Such an electrical connector may comprise a contact ring 46 or, in the illustrated embodiment, a plurality of contact rings $46_{1-N}$. The contact rings $46_{1-N}$ may be configured to electrically connect the medical device 36 (i.e., electrically-operable objects thereof, such as location sensing coil 44) to a corresponding electrical apparatus, such as the MPS 20 and/or the main control unit 12. In one embodiment, for example, the plurality of contact rings $46_{1-N}$ at the proximal end 42 may be configured as a male connector configured to be inserted into a corresponding female connector (not shown) that is in electrical communication with an external apparatus, such as the MPS 20 and/or the control unit 12. In an embodiment, other than with respect to the particular trace to which a contact ring is electrically connected, the plurality of contact rings $46_{1-N}$ are electrically insulated on an underside thereof with respect to the traces that lead to the electrical infrastructure 48 for further connection to the distal end of the medical device 36.

The electrical infrastructure 48 (shown in block form in FIG. 3) is configured to allow electrically communication between one electrical object, such as the location sensing coil 44 at the distal end 40, and another electrical object, such as the contact rings $46_{1-N}$ at the proximal end 42. Electrical infrastructure 48 may be located on body 38 of medical device 36, in a lumen of body 38 of medical device 36, and may be directly formed on body 38, such as an interior or exterior wall of body 38. Additionally, a plurality of electrical infrastructures 48 may be located in combination on various portions of the medical device 36.

In the illustrated embodiment of FIG. 3, the electrical infrastructure 48 is configured to (i) electrically connect contact ring $46_1$ to a first conductor end 94 of the location sensing coil 44; (ii) electrically connect contact ring $46_2$ to an electrically-conductive shield layer (shown in FIG. 4 as layer $78_2$); and (iii) electrically connect contact ring $46_N$ to a second conductor end 96 of the location sensing coil 44. These manner of these electrical connects will be described and illustrated in greater detail below in connection with FIG. 4.

Figure 4:
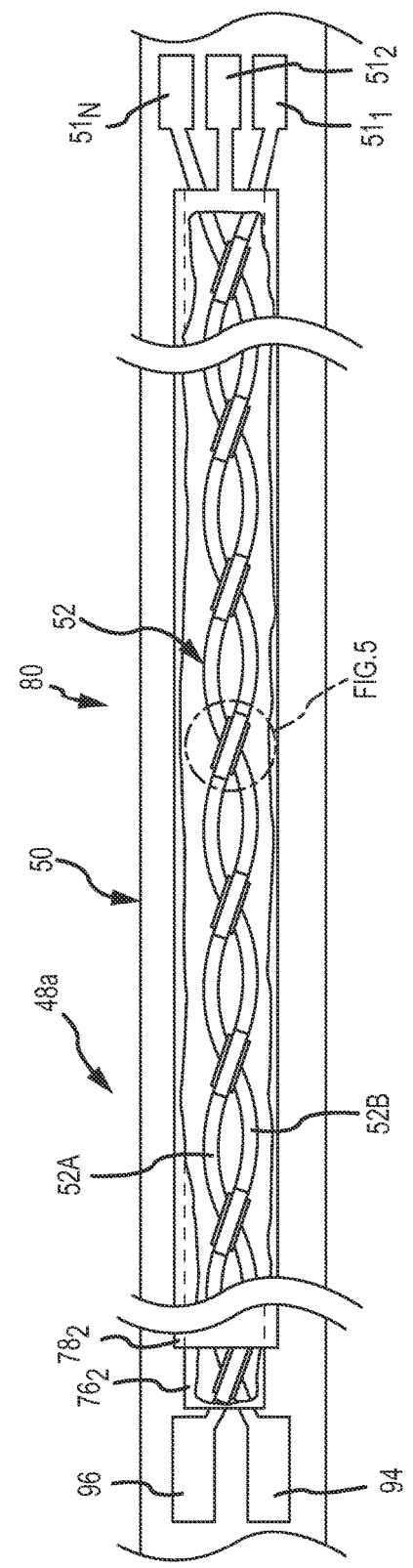
FIG. 4 is a diagrammatic top view showing in greater detail, the embodiment of the formed electrical infrastructure of FIG. 3.

FIG. 4 is a diagrammatic top view, with portions broken away, of further embodiment of an electrical infrastructure, designated infrastructure 48a. The electrical infrastructure 48a is configured to provide electrical pathways to allow transmission of electrical signals from the distal end 40 of the medical device 36 to the proximal end 42 of the medical device 36. In general, a device like the medical device 36 may use tiny electrical cables (i.e., conventional twisted pair (TP) cable) that may be expensive to manufacture, hard to handle, mechanically sensitive, and in some instances too "big" to implement in such devices with limited space without significantly affecting the mechanical properties of the device. As currently disclosed, however, embodiments of an electrical infrastructure consistent with the teachings herein provide various advantages, such as using reduced space, being potentially less expensive to manufacture, and potentially minimizing or eliminating the need for handling during production of the medical device into which it is incorporated.

The electrical infrastructure 48a may comprise a twisted pair of conductors, collectively designated 52, located on a substrate 50, such as the elongated body 38 of the medical device 36. The pair of conductors 52 include electrically separate conductors—designated $52_A$, $52_B$—that are "twisted" about each other. As used herein, "twisted" conductors may refer to conductors that are inter-woven, alternated, braided, twisted, or otherwise comprising such a configuration. The "twist" of the conductors $52_A$, $52_B$, helps reject electromagnetic noise that might otherwise be picked up by the conductors $52_A$, $52_B$. In an embodiment, the twisted pair of conductors 52 may be formed through a process (described in greater below) forming a first layer of electrically conductive material 54, a second layer of electrically nonconductive material 56, and a third layer of electrically conductive material 58. Each subsequent layer may be formed over at least a portion of the preceding layer in a manner described below.

In an embodiment, the conductive and nonconductive materials may be an electrically conductive ink or electrically nonconductive ink, respectively. The conductive and nonconductive materials may be formed by depositing or printing directly on a surface, such as the substrate 50, and directly over pre-existing layers of existing conductive and nonconductive materials. The conductive and nonconductive materials may be formed directly on components of the medical device 36 using technologies such as ink jet printing, pad printing, aerosol jet deposition that may be known in the art as aerosol jet printing (AJP), three-dimensional (3D) micro-printing, and other printing technologies as known to those of skill in the art.

In an embodiment, the substrate 50 may comprise an outer surface of the elongated body 38 of the medical device 36. In another embodiment, the substrate 50 may comprise a separate component from the elongated body 38 that is configured to attach to the medical device 36, either on the body 38 or within a lumen of the body 38 of the medical device 36. The three dimensional layering of conductive and nonconductive materials may be formed in a predetermined pattern and/or configuration to provide end-to-end electrical connectivity.

The electrical infrastructure 48a may comprise, as described above, conductors designated $52_A$ and $52_B$ disposed on the substrate 50. The conductors $52_A$, $52_B$ are electrically isolated from each other and are formed in an inter-woven, alternating, braided, or twisted arrangement (hereinafter "twisted pair" 52). The twisted pair 52 may have a multi-layered construction of conductive layers and non-conductive layers stacked upon each other to replicate the twisting of a pair of wires that exists in a conventional twisted pair (TP) cable.

The electrical infrastructure 48a includes the twisted pair of conductors 52 as described above may be formed as a shielded twisted pair of conductors, designated by reference numeral 80, as shown in FIG. 4, and as further shown in FIG. 6C. The shielding function can be implemented by including an isolation layer 76 and a shielding layer 78. In this regard, the substrate 50 comprises (i) lower isolation and shielding layers ($76_1$, $78_1$ best shown in FIG. 6C), which are formed underneath the twisted pair of conductors 52; and (ii) upper isolation and shielding layers $76_2$, $78_2$, which are formed on top of the twisted pair of conductors 52. In FIG. 4, the upper isolation layer 76$_2$, and the upper shielding layer 78$_2$, have been partially broken away to show the twisted pair of conductors 52.

With continued reference to FIG. 4, an electrically conductive trace 51$_1$ is electrically coupled to conductor 52B, which is further electrically connected to the first conductor end 94 of the location sensing coil 44. In addition, an electrically conductive trace 51$_2$ is electrically connected to shielding layer 78$_2$, which may be coupled to a ground or reference node. Finally, an electrically conductive trace 51$_N$ is electrically coupled to conductor 52$_A$, which is further electrically connected to the second conductor end 96 of the location sensing coil 44. The electrically conductive traces 51$_1$, 51$_2$, 51$_N$ may be electrically connected to contact rings 46$_1$, 46$_2$, 46$_N$, as shown in FIG. 3.

FIG. 5 generally illustrates an enlarged view of one of the multiple intersections of conductor 52$_A$ and conductor 52$_B$ shown in FIG. 4. It should be understood that the description of the conductors 52A, 52B applies with equal force to both shielded and unshielded twisted pair embodiments. In an embodiment, twisted pair 52 may comprise a first layer of conductive material 54, a second layer of nonconductive material 56, and a third layer of conductive material 58. First layer of conductive material 54 may comprise a plurality of electrically conductive segments 60 separated by a gap 62. For example, three segments 60$_1$, 60$_2$, 60$_3$ are illustrated in FIG. 5. A first segment 60$_1$ and a second segment 60$_2$ are separated by gap 62. A third segment 60$_3$ traverses through gap 62 without contacting first segment 60$_1$ and second segment 60$_2$. In order to connect first segment 60$_1$ to second segment 60$_2$ without touching third segment 60$_3$, second layer of nonconductive material 56 is located in gap 62 to directly cover a portion of third segment 60$_3$. Second layer of nonconductive material 56 comprises an insulator masking 64 configured to electrically insulate a portion of third segment 60$_3$ located in gap 62. Third layer of conductive material 58 may then be located directly on second layer of nonconductive material 56. Third layer of conductive material 58 may comprise a conductive bridge 70 configured to electrically connect first segment 60$_1$ to second segment 60$_2$ while remaining electrically isolated from third segment 60$_3$ because of insulator masking 64.

While FIG. 5 generally illustrates one of the multiple intersections of electrical infrastructure 48a, the above described structure may be repeated throughout the remaining intersections. The resultant structure allows conductor 52$_A$ to cross the path of conductor 52$_B$ in a twisted arrangement while remaining electrically isolated from each other.

Figure 7:
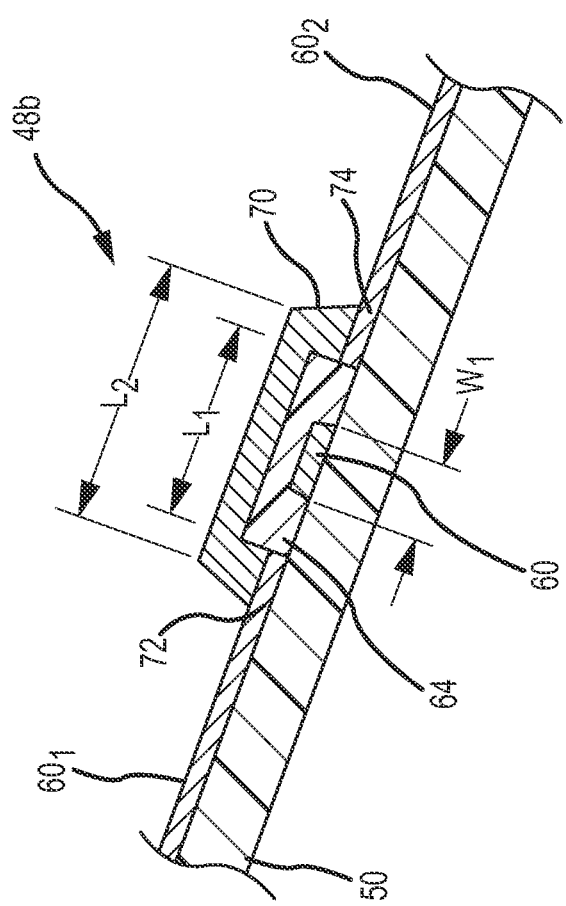
FIG. 7 is a cross-sectional view taken substantially along lines 7-7 in FIG. 5.

FIGS. 6A and 7 are cross-sectional views of a further embodiment of an electrical infrastructure, designated infrastructure 48b, taken substantially along lines 6A-6A and 7-7 in FIG. 5, respectively. The infrastructure 48b, as illustrated, is unshielded and is formed on the substrate 50. To replicate the twisted configuration of a conventional TP cable in a layered structure, the insulator masking 64 separates the conductor 52$_A$ and the conductor 52$_B$ in the intersection of the two conductors. As illustrated, the twisted pair 52 comprises stacked layers formed on top of each other to allow the conductor 52$_A$ and the conductor 52$_B$ to cross without electrically contacting each other. For example, the third segment 60$_3$ of the first layer of conductive material 54 may be located on the substrate 50. The insulator masking 64 of the second layer of nonconductive material 56 may be located on a portion of the third segment 60$_3$ such that a top surface 66 and side surfaces 68 of the third segment 60$_3$ are electrically insulated by nonconductive material. A bridge 70 of the third layer of conductive material 58 may be located on the insulator masking 64. By providing nonconductive material between the first layer of conductive material 54 and the third layer of conductive material 58, the conductor 52$_A$ and the conductor 52$_B$ may cross without contacting each other.

In an exemplary embodiment of electrical infrastructure 48b, the distance D between an edge of the conductor 52$_A$ and an edge of the conductor 52$_B$ may be about 0.1 mm. The segments 60 may have a width $W_1$ of about 0.04 mm and a thickness $T_1$ of about 0.002 mm. The insulator maskings 64 may have a width that is wider than the width $W_1$ of segments 60. Insulator maskings 64 may have a general thickness $T_2$ of about 0.001 mm and a length $L_1$ of about 0.05 mm. The length $L_1$ of the insulator maskings 64 may be about the same size as the span of the gaps 62. The conductive bridges 70 may have a width $W_2$ of about 0.04 mm, and may be generally the same width as the segments 60. The conductive bridges 70 may have a thickness $T_3$ of about 0.002 mm and a length $L_2$ of about 0.095 mm. The length $L_2$ of conductive bridges 70 may be configured such that conductive bridges 70 are longer than the insulator maskings 64. While various dimensions of the disclosed layers of twisted pair 52 have been provided in detail, it will be appreciated that this disclosure is not so limited. Rather, other dimensions may be utilized as known to those with skill in the art and remain within the scope and spirit of this disclosure.

FIG. 6B is a cross-sectional view of a further embodiment of an electrical infrastructure, designated infrastructure 48c. In particular situations, it may be desirable to electrically insulate the twisted pair of conductors, and thus electrical isolation layers are provided for such purpose. For example, the substrate 50 may be an electrically conductive material and therefore the twisted pair of conductors 52 would need to be electrically isolated from the underlying substrate 50. Additionally, insulating the twisted pair of conductors 52 may also provide physical protection to the electrical infrastructure 48c.

The insulated twisted pair of conductors of infrastructure 48c may comprise the twisted pair of conductors 52, as described above, but further surrounded by electrical isolation layers 76 of electrically insulating (i.e., electrically nonconductive) material. Isolation layers 76 may comprise a lower isolation layer 76$_1$ and an upper isolation layer 76$_2$. The lower isolation layer 76$_1$ may be positioned onto an upper surface of the substrate 50. The twisted pair of conductors 52 may then be positioned onto an upper surface of the lower isolation layer 76$_1$. After the twisted pair of conductors 52 have been formed on lower isolation layer 76$_1$, then the upper isolation layer 76$_2$ may be positioned over and formed on the twisted pair of conductors 52 and the upper surface of the lower isolation layer 76$_1$. The isolation layers 76 may surround an intermediate portion of the twisted pair of conductors 52. For example, the ends of conductors 52$_A$, 52$_B$ may not be covered by the isolation layers 76. The ends of the conductors 52$_A$, 52$_B$ may be configured to connect to electrical objects (e.g., location sensing coil 44) located at or near the distal end 40, on the one hand, and objects at or near the proximal end 42 of the medical device 36, on the other hand (e.g., contact ring 46). In an embodiment where the substrate 50 is a nonconductive material, the lower isolation layer 76$_1$ may not be necessary. In other words, the twisted pair of conductors 52 may be formed directly onto the substrate 50, and then the upper isolation layer 76$_2$ may be placed on top of the twisted pair of conductors 52 and the substrate 50. In an exemplary embodiment, a width $W_3$ of both the lower isolation layer $76_1$ and the upper isolation layer $76_2$ may be about 0.2 mm. A thickness $T_4$ of both the lower isolation layer $76_1$ and the upper isolation layer $76_2$ may be about 0.001 mm. While various dimensions of the isolation layers 76 have been provided in detail, it will be appreciated that this disclosure is not so limited. Rather, other dimensions may be utilized as known to those with skill in the art and remain within the scope and spirit of this disclosure.

FIG. 6C is a cross-sectional view of a still further embodiment of an electrical infrastructure, designated infrastructure 48d. The electrical infrastructure 48d may include, in addition to the twisted pair of conductors 52, both isolation and shielding layers so as to form a shielded twisted pair of conductors 80. In particular situations, it may be desirable to electrically shield the twisted pair of conductors 52. Electrical shielding 78 may reduce or eliminate electrical interference. Additionally, the electrical shielding 78 may provide physical protection to the twisted pair of conductors 52.

The shielded twisted pair of conductors 80 may comprise an insulated twisted pair of conductors 52, such as in FIG. 6B, but further surrounded by a plurality of shield layers 78 comprising electrically conductive material. The shield layers 78 may be configured to act as an electrical shield for the twisted pair of conductors 52, forming the shielded twisted pair of conductors 80. The shield layers 78 may comprise a lower shield layer $78_1$ and an upper shield layer $78_2$. In an embodiment, the lower shield layer $78_1$ may be located directly on a surface of the substrate 50. As generally illustrated, the substrate 50 does not need to be a flat planar surface. Rather, the substrate 50 may have a curved surface or contoured surface, and twisted pair of conductors 52, whether or not insulated, and whether or not shielded, may be formed directly on the curved or contoured surface, such as but not limited to, the tubular body 38 of the medical device 26. The lower isolation layer $76_1$ may be located on the lower shield layer $78_1$. The formed twisted pair 52 may be located on the lower isolation layer $76_1$. The upper isolation layer $76_2$ may be located over the formed twisted pair of conductors 52 and the lower isolation layer $76_1$. The upper shield layer $78_2$ may be located over the upper isolation layer $76_2$. The lower layer $78_1$ and the upper layer $78_2$ may be in electrical contact with each other. In an exemplary embodiment, both the lower layer $78_1$ and the upper layer $78_2$ may have a width $W_4$ of about 0.4 mm and a thickness $T_5$ of about 0.002 mm. While various dimensions of the shield layers 76 have been provided in detail, it will be appreciated that this disclosure is not so limited. Rather, other dimensions may be utilized as known to those with skill in the art and remain within the scope and spirit of this disclosure.

While the shielded twisted pair 80 has been disclosed as having one twisted pair of conductors 52 within shielding 78, this disclosure is not so limited. Rather, the shielded twisted pair 80 may comprise a plurality of twisted pairs of conductors 52 located within the shielding layer 78.

Referring to FIGS. 8A-8G, a method of manufacturing an embodiment of the shielded twisted pair of conductors 80 of FIG. 6C will now be set forth. Each of the various figures generally illustrates a respective layer of an embodiment of the shielded twisted pair of conductors 80.

Figure 8A:
FIGS. 8A-8G are diagrammatic top views of layers of an embodiment of a twisted pair of conductors.
Figure 8B:
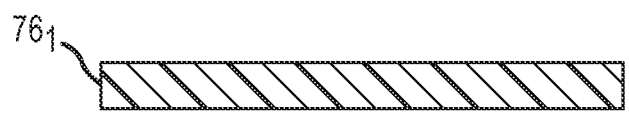

The lower shield layer $78_1$, generally illustrated in FIG. 8A, comprising electrically conductive ink may be formed onto the substrate 50. While the method refers to forming, any deposition technology of electrically conductive and electrically nonconductive materials as known to those with skill in the art may be utilized. The lower isolation layer $76_1$ (generally illustrated in FIG. 8B) comprising electrically nonconductive ink may be formed onto the lower shield layer $78_1$.

Figure 8C:
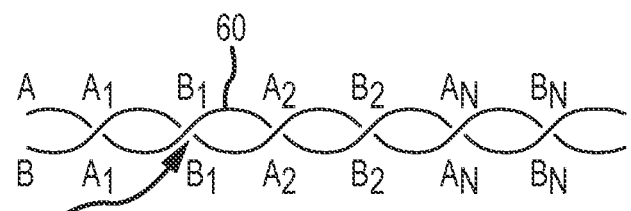

A base layer of plurality of segments 60 comprising electrically conductive ink may be formed on the lower isolating layer $76_1$ in a predetermined pattern. One embodiment of the predetermined pattern is generally illustrated in FIG. 8C, where the segments 60 are separated by gaps 62. The gaps 62 may have a span identified on FIG. 8C as $A_1$-$A_1$, $B_1$-$B_1$, $A_2$-$A_2$, $B_2$-$B_2$, . . . $A_N$-$A_N$, $B_N$-$B_N$. While a limited amount of gaps 62 and related span of the gap relative to segments 60 are generally illustrated, it will be appreciated that this disclosure is not so limited. Rather any number of segments 60 and gaps 62 may be utilized for a particular application of this disclosure as known to those with skill in the art. Adjacent segments 60 may cross paths via gaps 62 without touching other segments 60. While unconnected to any additional layers, each individual segment of the plurality of segments 60 is electrically isolated from the other segments 60. The segments 60 may be, in non-limiting, exemplary embodiments, generally sinusoidal shaped, or in other words, "S" shaped or lazy-"S" shaped.

Figure 8D:
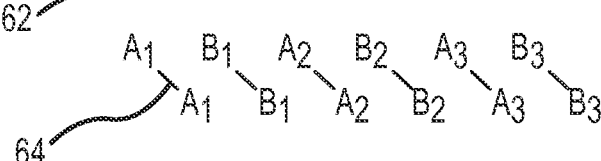

A plurality of the insulator maskings 64 comprising electrically nonconductive ink may be formed in the gaps 62 between the segments 60. The insulator maskings 64 may cover a portion of the segments 60 located in the gaps 62. As generally illustrated in FIG. 8D, the insulator maskings 64 may be located in the gaps 62 having spans $A_1$-$A_1$, $B_1$-$B_1$, $A_2$-$A_2$, $B_2$-$B_2$, . . . $A_N$-$A_N$, $B_N$-$B_N$.

The insulator maskings 64 may cover portions of a top surface 66 and side surfaces 68 of the segments 60. The insulator maskings 64 may be configured to electrically insulate the conductor $52_A$ from the conductor $52_B$.

Figure 8E:
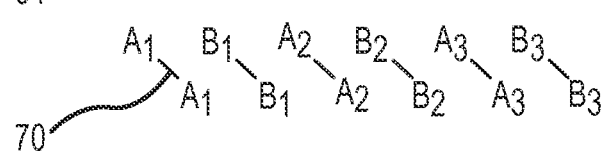
Figure 8F:
Figure 8G:

A plurality of conductive bridges 70 comprising electrically conductive ink may be formed on the insulator maskings 64 to electrically connect adjacent segments 60. As generally illustrated in FIG. 8E, the conductive bridges 70 may be located in the gaps 62 and a portion of the ends of the segments 60 from spans $A_1$-$A_1$, $B_1$-$B_1$, $A_2$-$A_2$, $B_2$-$B_2$, . . . $A_N$-$A_N$, $B_N$-$B_N$.

The upper isolation layer $76_2$ (generally illustrated in FIG. 8F) comprising electrically nonconductive ink may be formed onto the layers of segments 60, insulator maskings 64, conductive bridges 70, and lower shield layer $78_1$. The upper shield layer $78_2$ (generally illustrated in FIG. 8G) comprising electrically conductive ink may be formed onto the upper isolation layer $76_2$ and the lower shield layer $78_1$. The upper shield layer $78_2$ may be electrically connected to the lower shield layer $78_1$.

FIG. 9 generally illustrates a cross-sectional view of yet another embodiment of an electrical infrastructure, designated electrical infrastructure 48e. A three-dimensional layered electrical infrastructure 48e may comprise lower shield layer $78_1$, lower isolation layer $76_1$, a first circuit layer 82, an insulation layer 84, a second circuit layer 86, upper isolation layer $76_2$, and upper shield layer $78_2$. In an embodiment, each of the layers may be formed upon the proceeding layer.

For example, in an exemplary embodiment, the lower shield layer $78_1$ comprising electrically conductive material may be formed onto the substrate 50. The lower shield layer $78_1$ may have width $W_4$ of about 0.4 mm and thickness $T_5$ of about 0.002 mm. The lower isolation layer $76_1$ comprising electrically nonconductive material may be formed onto the lower shield layer $78_1$. The lower isolation layer $76_1$ may have width $W_3$ of about 0.15 mm and thickness $T_4$ of about 0.001 mm. The first circuit layer 82 comprising electrically conductive material may be formed onto the lower isolation layer $76_1$. The first circuit layer 82 may have width $W_2$ of about 0.06 mm and thickness $T_1$ of about 0.002 mm. The insulation layer 84 comprising electrically nonconductive material may be formed onto the first circuit layer 82 and the lower isolation layer $76_1$. The insulation layer 84 may have width $W_5$ of about 0.08 mm and thickness $T_4$ of about 0.001 mm. The second circuit layer 86 comprising electrically nonconductive material may be formed onto the insulation layer 84. The second circuit layer 86 may have width $W_2$ of about 0.06 mm and thickness $T_4$ of about 0.002 mm. The upper isolation layer $76_2$ comprising electrically nonconductive material may be formed onto the second circuit layer 86 and the insulation layer 84. The upper isolation layer $76_2$ may have width $W_3$ of about 0.15 mm and thickness $T_4$ of about 0.001 mm. The upper shield layer $78_2$ comprising electrically conductive material may be formed onto the upper isolation layer $76_2$ and the lower shield layer $78_1$. In an embodiment, the upper shield layer $78_2$ may have width $W_4$ of about 0.4 mm and thickness $T_5$ of about 0.002 mm. The distal and proximal ends of the first circuit layer 82 and the second circuit layer 86 may be configured to electrically connect to electrically operated objects located on the medical device 36. While various dimensions of the layers have been provided in detail, it will be appreciated that this disclosure is not so limited. Rather, other dimensions for the layers may be utilized as known to those with skill in the art and remain within the scope and spirit of this disclosure.

Additionally, while an embodiment disclosing two electrically conductive circuit layers has been described in detail, it will be appreciated that this disclosure is not so limited. Rather, various embodiments of an electrical infrastructure consistent with the teachings disclosed herein may comprise any number of electrically conductive circuit layers as necessary for a particular application and remain within the scope and spirit of this disclosure. For example, an embodiment of an electrical infrastructure may comprise only one circuit layer, whereas another embodiment of an electrical infrastructure may be configured to perform like a coaxial cable. A still further embodiment of an electrical infrastructure may comprise a plurality of circuit layers as may be necessary to transmit electrical signals from an electrically operable object located on or at the distal end 40 to the proximal end 42 of the medical device 36.

FIGS. 10A and 10B are enlarged, partial cross-sectional views, with portions broken away, of embodiments of the location sensing coil 44 of FIG. 3, designated location sensing coils 44a and 44b, respectively. Location sensing coils 44a, 44b, may be disposed proximate the distal end 40 of the medical device 36. The location sensing coil 44 may be configured as an electromagnetic coil position sensor for device navigation in various medical procedures. In an embodiment, the location sensing coils 44a, 44b, may be formed directly on the distal end 40 of the medical device 36 as described further herein. In addition, the location sensing coil 44 of FIG. 3 may alternatively be formed as described in U.S. application Ser. No. 13/232,536, filed 14 Sep. 2011 (the '536 application), now pending, and U.S. application Ser. No. 13/341,396, filed 30 Dec. 2011 (the '396 application), now pending. The '536 application and the '396 application are both hereby incorporated by reference as though fully set forth herein.

FIG. 10A shows the location sensing coil 44a, which may include a core layer 88 comprising magnetically permeable material. The core layer 88 may be formed directly on the substrate 50, such as the tubular body 38 of the medical device 36, or mechanically wound around a circumferential surface of the substrate 50. The core layer 88 may confine and guide a magnetic field and amplify it by a certain factor. The core layer 88 may comprise a ferromagnetic material, such as but not limited to, μ-Metal. An insulative layer 90, which comprises electrically nonconductive material, may be directly formed on the core layer 88 by printing or other ink deposition technologies as known to those with skill in the art. A single layer coil 92 may be formed on the insulative layer 90 in a predefined pattern. In another embodiment, when the substrate 50 comprises nonconductive material, the single layer coil 92 may be formed directly onto the substrate 50 without need for the insulative layer 90 and may comprise electrically conductive material. The pattern may be generally spiral shaped around the core layer 88 or the substrate 50. In an exemplary and non-limiting embodiment, the single layer coil 92 may have a width $W_6$ of between about 0.0059-0.060 mm and a thickness $T_6$ of between about 0.001-0.003 mm. In an exemplary and non-limiting embodiment, the single layer coil 92 a distance between the conductor material as it spirals about the core layer 88, also known as a pitch P, of between about 0.005-0.060 mm. In an exemplary and non-limiting embodiment, the single layer coil 92 may have a skew angle α as the conductor material spirals about the coil of about up to 45 degrees (skew angle α is generally illustrated in FIG. 3).

FIG. 10B shows the location sensing coil 44b, which has a plurality of layers, designated $92_1, 92_2, \ldots, 92_N$ wherein N=the number of layers in the location sensing coil 44b, and which comprises electrically conductive material. Each layer $92_{1-N}$ of location sensing coil 44b may be separated by a respective insulative layer 90. In an embodiment, each of the single layer coils may be electrically connected to each other. In another embodiment, each of the single layer coils may be electrically connected to a corresponding twisted pair of conductors 52.

As generally illustrated in FIG. 3, the single layer coil 92 or multiple layer coil $92_{1-N}$ (when the layers are electrically connected in series) may have a first conductor end 94 and a second conductor end 96. The first conductor end 94 and second conductor end 96 may be electrically connected to the electrical infrastructure 48 for signal transmission, for example the electrical infrastructure 48d that includes the shielded twisted pair of conductors 80. In an embodiment, a layer of nonconductive material 98 may be formed over a portion of the location sensing coil 44 to allow the second conductor end 96—which would otherwise terminate at the distal end of the location sensing coil 44, to be routed across coil 44 without electrically shorting the single layer coil 92. As a result, both the first and second conductor ends 94, 96 present at the proximal end of the location sensing coil 44.

As also generally illustrated in FIG. 3, the proximal end of the electrical infrastructure 48 may be connected to contact ring 46, or the plurality of contact rings $46_{1-N}$ located proximate the proximal end 42 of medical device 36. In embodiments, contact ring 46 may comprise three-dimensional structural layering of conductive material and non-conductive material using methods as previously described above. For example, contact ring $46_1$ may comprise a layer of conductive material. A layer of insulative material may be formed, with respect to one or more of the contact rings $46_{1-N}$, which allows other circuits from electrical infrastructure 48 (e.g., traces) to cross one or more of the contact rings $46_{1-N}$ without electrically shorting out on any particular contact ring (i.e., other than a particular trace that is intended to be electrically connected to a particular contact ring). The other circuits may connect to contact rings $46_{2-N}$.

Figure 11:
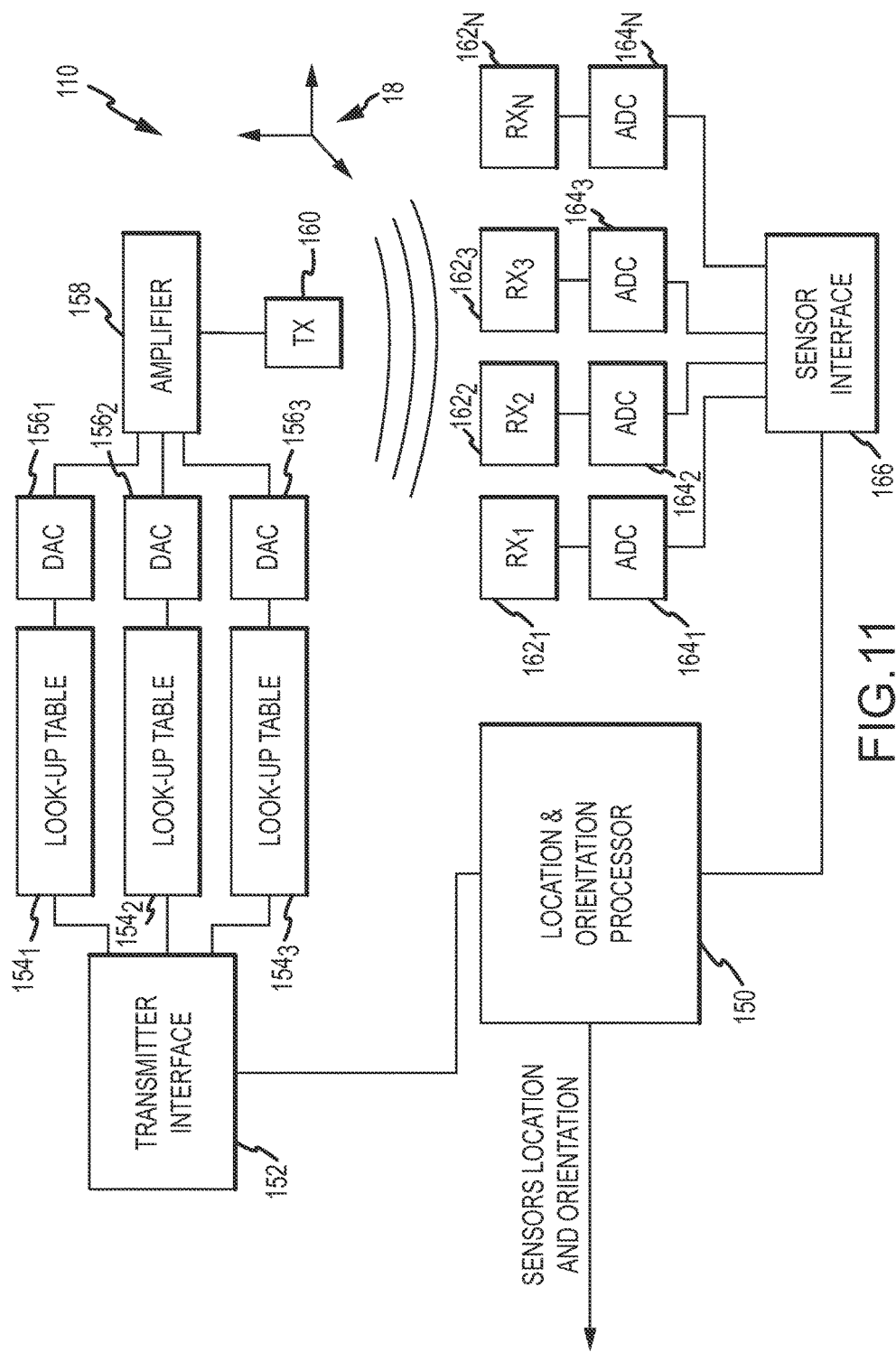
FIG. 11 is a schematic and block diagram view of one exemplary embodiment of a medical positioning system (MPS) as shown in block form in FIG. 1.

FIG. 11 is a schematic and block diagram of one exemplary embodiment of MPS 20, designated as a MPS 110, as seen by reference to U.S. Pat. No. 7,386,339, hereby incorporated by reference as though fully set forth herein, having portions of which are reproduced below, which generally describes, at least in part, the MediGuide™ Technology system commercially offered by MediGuide Ltd. of Haifa, Israel and now owned by St. Jude Medical, Inc. It should be understood that variations are possible, for example, as also seen by reference to U.S. Pat. No. 6,233,476, hereby incorporated by reference as though fully set forth herein. Another exemplary magnetic field-based MPS is the Carto™ system commercially available from Biosense Webster, and as generally shown and described in, for example, U.S. Pat. Nos. 6,498,944, and 6,788,967, both hereby incorporated by reference as though fully set forth herein. Accordingly, the following description is exemplary only and not limiting in nature.

MPS 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly the main electronic control unit 12, as described above may include conventional processing apparatus known in the art, capable of executing pre-programmed instructions stored in an associated memory, all performing in accordance with the functionality described herein. Such an electronic control unit may further be of the type having both ROM, RAM, a combination of non-volatile and volatile (modifiable) memory so that any software may be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from this disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for manufacturing an electrical infrastructure of a medical device, said method comprising:
    printing a base layer comprising electrically conductive material in a predefined pattern by depositing an electrically conductive ink on a surface of the medical device, wherein printing said predefined pattern of said base layer comprises forming a plurality of sinusoidal-shaped segments separated by a plurality of gaps wherein each sinusoidal-shaped segment does not contact the other sinusoidal-shaped segments;
    printing a masking layer comprising electrically nonconductive material directly over a portion of said first layer of conductive material by depositing an electrically nonconductive ink, wherein printing said masking layer comprises depositing nonconductive ink in said gaps to electrically insulate a portion of said segments positioned within said gaps; and
    printing a bridge layer comprising electrically conductive material directly over a portion of said base layer and a portion of said masking layer by depositing electrically conductive ink,
    wherein said plurality of gaps comprises a first plurality of gaps and a second plurality of gaps different from said first plurality of gaps and wherein forming said plurality of sinusoidal-shaped segments comprises forming first sinusoidal-shaped segments separated by said first plurality of gaps and forming second sinusoidal-shaped segments different from said first sinusoidal-shaped segments where said second sinusoidal-shaped segments are separated by said second plurality of gaps and wherein said second sinusoidal-shaped segments are positioned within said first plurality of gaps, and wherein said printing said bridge layer comprises depositing said electrically conductive ink in said first and second plurality of gaps so as to electrically connect said first sinusoidal-shaped segments to form a first electrical conductor and to electrically connect said second sinusoidal-shaped segments to form an electrically separate second electrical conductor to thereby form an electrically separate and isolated pair of conductors in a twisted configuration.

2. The method of claim 1 further comprising printing an upper isolation layer comprising electrically nonconductive material and a lower isolation layer comprising electrically nonconductive material, wherein said upper isolation layer and said lower isolation layer together surround said twisted pair of conductors.

3. The method of claim 2 wherein printing said upper and lower isolation layers comprise depositing electrically nonconductive ink.

4. The method of claim 2 further comprising printing an upper shield layer comprising electrically conductive material and a lower shield layer comprising electrically conductive material, wherein said upper shield layer and said lower shield layer together surround an insulated twisted pair of conductors comprising said twisted pair of conductors and said upper and lower isolation layers.

5. The method of claim 4 wherein printing said upper and lower shield layers includes completely surrounding said insulated twisted pair of conductor to electrically shield said insulated twisted pair of conductors.

6. The method of claim 4, wherein printing said upper and lower shield layers comprise depositing electrically conductive ink.

7. The method of claim 4, wherein said twisted pair of conductors extend along an axis, and wherein said printing said upper and lower isolation layers comprises depositing nonconductive ink over a longitudinally intermediate section of said twisted pair of conductors thereby leaving longitudinal ends of said twisted pair of conductors uncovered.

8. The method of claim 1 further comprising:
providing said surface of said medical device as an elongate, tubular member comprising electrical insulating material.

9. The method of claim 8 wherein printing of said base layer of said twisted pair of conductors extends from about a distal end to about a proximal end of said elongate tubular member.

10. The method of claim 1 further comprising:
providing a coil by printing a coil layer comprising a length of spirally-wound electrically conductive material, wherein said coil layer comprises one continuous electric circuit having a first end and a second end, said first and second ends of said coil being electrically connected to said twisted pair of conductors.

11. The method of claim 10 further comprising:
providing a core comprising magnetically-permeable material wherein said coil layer extends through a path spiraling around said core.

12. The method of claim 10 wherein providing said coil comprises printing a plurality of coil layers wherein each of said coil layers are separated by an electrically insulative layer comprising nonconductive ink configured to electrically isolate adjacent coil layers.

13. A method for manufacturing an electrical infrastructure of a medical device, said method comprising:
printing a base layer comprising electrically conductive material in a predefined pattern by depositing an electrically conductive ink on a surface of the medical device;
printing a masking layer comprising electrically nonconductive material directly over a portion of said first layer of conductive material by depositing an electrically nonconductive ink;
printing a bridge layer comprising electrically conductive material directly over a portion of said base layer and a portion of said masking layer by depositing electrically conductive ink wherein said printing said base layer and said bridge layer are performed so as to form a twisted pair of conductors;
printing an upper isolation layer comprising electrically nonconductive material and a lower isolation layer comprising electrically nonconductive material, wherein said upper isolation layer and said lower isolation layer together surround said twisted pair of conductors; and
printing an upper shield layer comprising electrically conductive material and a lower shield layer comprising electrically conductive material, wherein said upper shield layer and said lower shield layer together surround an insulated twisted pair of conductors comprising said twisted pair of conductors and said upper and lower isolation layers.

14. A method for manufacturing an electrical infrastructure of a medical device, said method comprising:
printing a base layer comprising electrically conductive material in a predefined pattern by depositing an electrically conductive ink on a surface of the medical device;
printing a masking layer comprising electrically nonconductive material directly over a portion of said first layer of conductive material by depositing an electrically nonconductive ink;
printing a bridge layer comprising electrically conductive material directly over a portion of said base layer and a portion of said masking layer by depositing electrically conductive ink wherein said printing said base layer and said bridge layer are performed so as to form a twisted pair of conductors;
printing an upper isolation layer comprising electrically nonconductive material and a lower isolation layer comprising electrically nonconductive material, wherein said upper isolation layer and said lower isolation layer together surround said twisted pair of conductors;
printing an upper shield layer comprising electrically conductive material and a lower shield layer comprising electrically conductive material, wherein said upper shield layer and said lower shield layer together surround an insulated twisted pair of conductors comprising said twisted pair of conductors and said upper and lower isolation layers; and
providing a coil by printing a coil layer comprising a length of spirally-wound electrically conductive material, wherein said coil layer comprises one continuous electric circuit having a first end and a second end, said first and second ends of said coil being electrically connected to said twisted pair of conductors.

* * * * *